US006716577B1

(12) United States Patent
Yu et al.

(10) Patent No.: US 6,716,577 B1
(45) Date of Patent: Apr. 6, 2004

(54) ELECTROCHEMICAL TEST STRIP FOR USE IN ANALYTE DETERMINATION

(75) Inventors: Yeung Siu Yu, Pleasanton, CA (US); Mahesh Shah, Santa Clara, CA (US)

(73) Assignee: LifeScan, Inc., Milpitas, CA (US)

( * ) Notice: Subject to any disclaimer, the term of this patent is extended or adjusted under 35 U.S.C. 154(b) by 0 days.

(21) Appl. No.: 09/497,269

(22) Filed: Feb. 2, 2000

(51) Int. Cl.[7] .............................. C12I 1/68; G01N 21/00; C12N 11/16; C12M 1/00
(52) U.S. Cl. .............................. 435/6; 435/7.1; 435/14; 435/25; 435/176; 435/289.1; 422/50; 422/55; 422/58; 422/62; 422/68; 204/403
(58) Field of Search .............................. 435/289.1, 14, 435/6, 25, 7.1, 176; 204/403; 422/50, 55, 58, 62, 68

(56) References Cited

U.S. PATENT DOCUMENTS

| | | | |
|---|---|---|---|
| 5,030,310 A | | 7/1991 | Wogoman |
| 5,708,247 A | * | 1/1998 | McAleer et al. ............ 204/403 |
| 5,762,770 A | * | 6/1998 | Pritchard et al. ........... 204/403 |
| 5,834,224 A | | 11/1998 | Ruger et al. .................... 435/14 |
| 5,869,001 A | * | 2/1999 | Backhaus et al. ............. 422/58 |
| 5,942,102 A | | 8/1999 | Hodges et al. .............. 205/775 |
| 5,972,199 A | | 10/1999 | Heller et al. ............. 205/777.5 |
| 6,306,584 B1 | * | 10/2001 | Bamdad ........................ 435/6 |

FOREIGN PATENT DOCUMENTS

| | | |
|---|---|---|
| EP | 0 971 036 A1 | 1/2000 |
| GB | 2 304 628 | 3/1997 |
| WO | 97/18465 | 5/1997 |
| WO | WO 99/19507 | 4/1999 |
| WO | 99/49307 | 9/1999 |

OTHER PUBLICATIONS

Mizutani et al "Glucose oxidase/polyioin comlex–bilayer membrane for eleminaiton of electroactive interferents in amperometric glucose sensor" *Analytica Chimica Acta*, 1998, 364: 173–179.*

Nunes et al., "Evaluation of a highly sensitive amperometric biosensor with low cholinesterase charge immobilized on a chemically modified carbon past electrode for trace determination of carbamates in fruit, vegetable and water samples," *Analytica Chimica Acta* 399:37–49 (1999).

Shimojo et al., "Electrochemical Assay System with Single Use Electrode Strip for Measuring Lactate in Whole Blood" *Clin Chem* 39(11):2312–2314 (1993).

Dalmia et al., "Electrochemical Behavior of Gold Electrodes Modified with Self–Assembled Monolayers with an Acidic End Group for Selective Detection of Dopamine," *J. Electroanalytical Chem.* (1997) 430: 205–214.

Nakashima et al., "Assembled Supported Monolayers of Synthetic Lipids on Gold Electrodes via 'Ion–Exchange Methods'," *J. Chem. Soc.* (1990) 12: 845–847.

Palacin et al., "Patterning with Magnetic Materials at the Micron Scale," *Chem. Mater.* (1996) 8:1316–1325.

\* cited by examiner

*Primary Examiner*—B. J. Forman
(74) *Attorney, Agent, or Firm*—Bret E. Field; Carol M. LaSalle; Bozicevic, Field & Francis, LLP

(57) ABSTRACT

Electrochemical test strips and methods for their use in the detection of an analyte in a physiological sample are provided. The subject test strips have a reaction zone defined by opposing metal electrodes separated by a thin spacer layer. The metal surface of at least one of the electrodes is modified by a homogenous surface modification layer made up of linear self-assembling molecules having a first sulfhydryl end group and a second sulfonate end group separated by a short chain alkyl linking group, where 2-mercaptoethane sulfonic acid or a salt thereof is preferred in certain embodiments. The subject electrochemical test strips find application in the detection of a wide variety of analytes, and are particularly suited for use the detection of gluose.

22 Claims, 6 Drawing Sheets

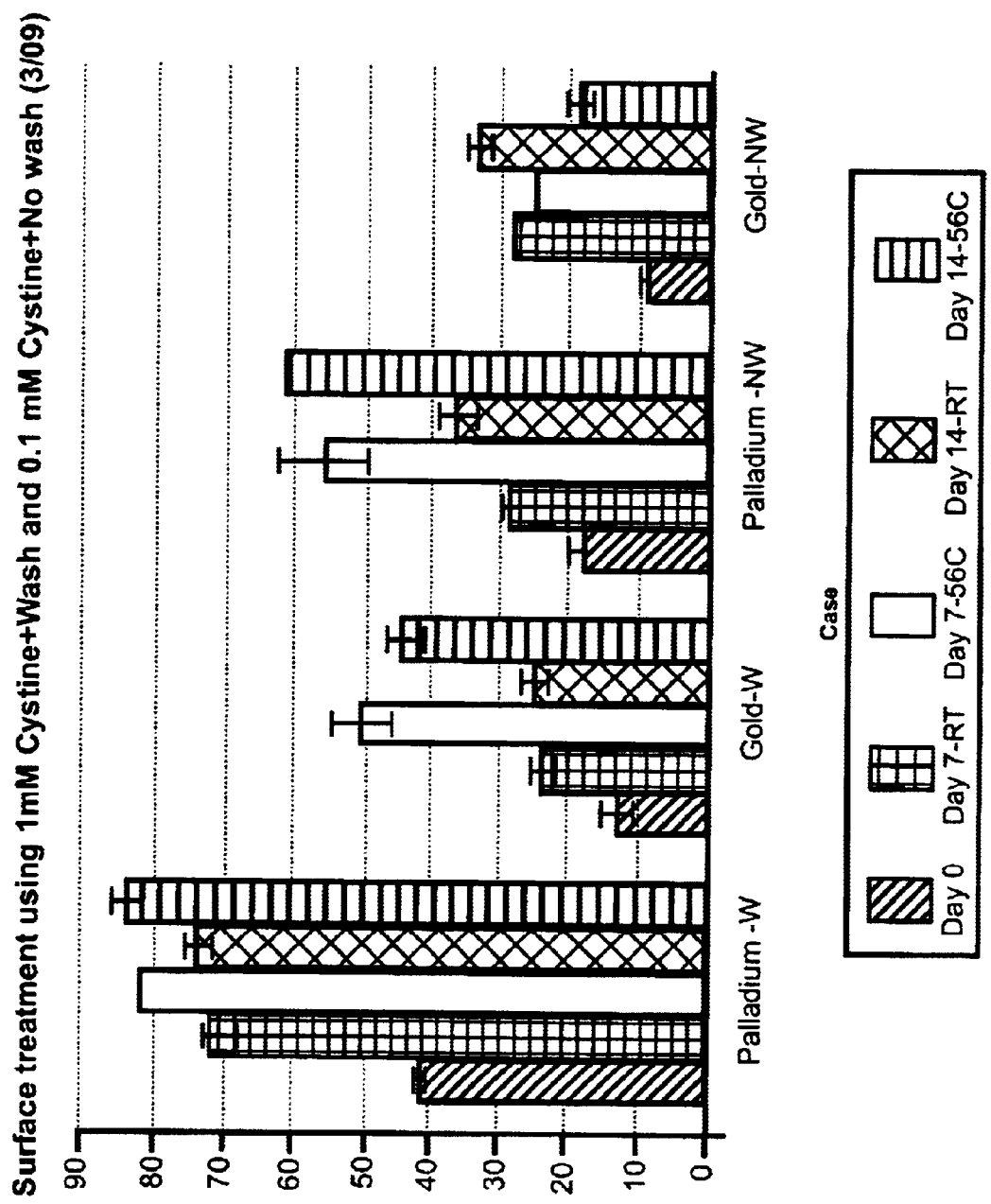

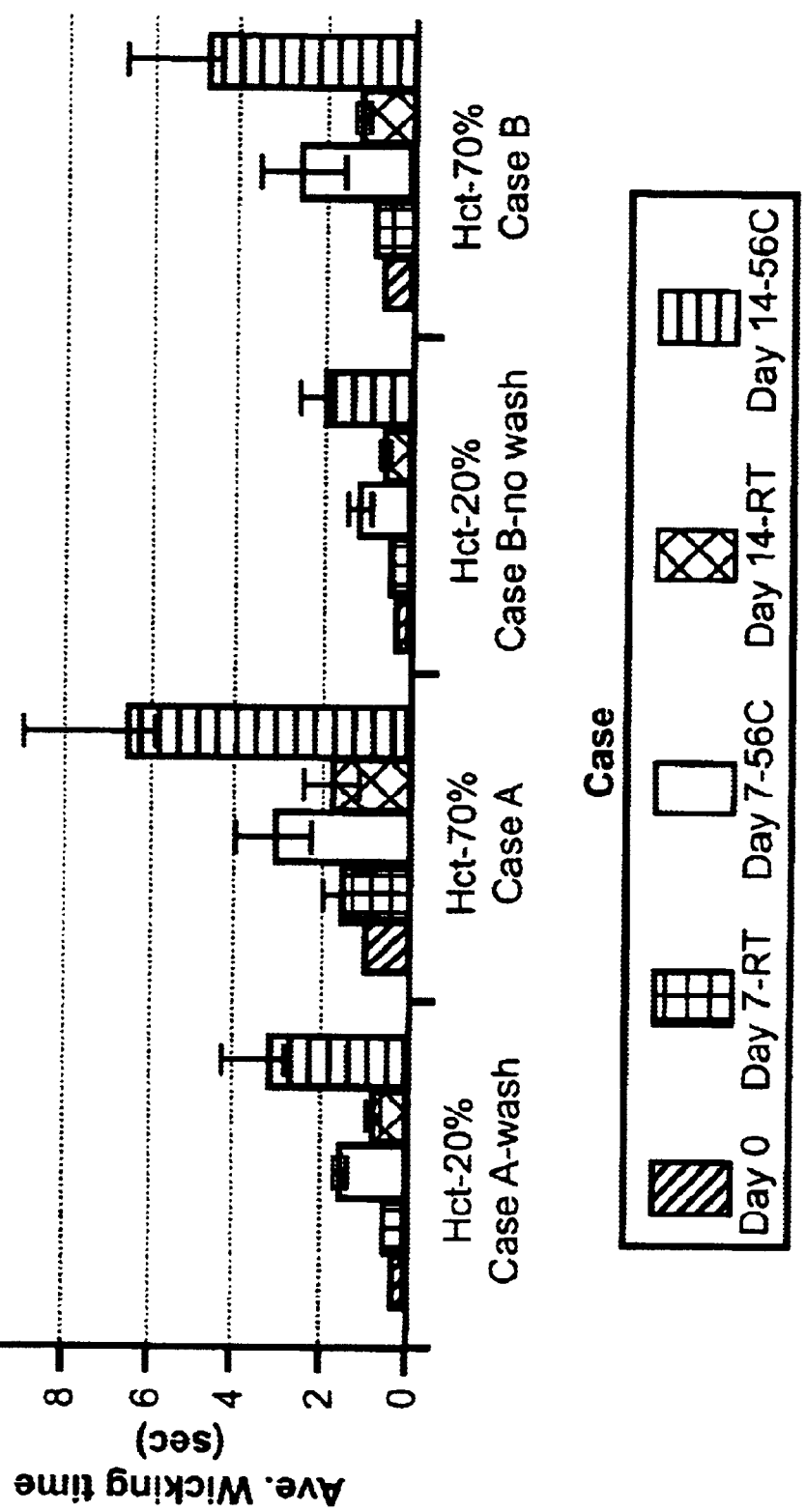

Aldrich MESA (98%) 0.1% @ pH 5.40, Surface treated Gold and Palladium with tape (ARI), hang dried n=5

Aldrich MESA (98%) 0.1% @ pH 11.5, Surface treated Gold and Palladium with tape (ARI), hang dried n=5

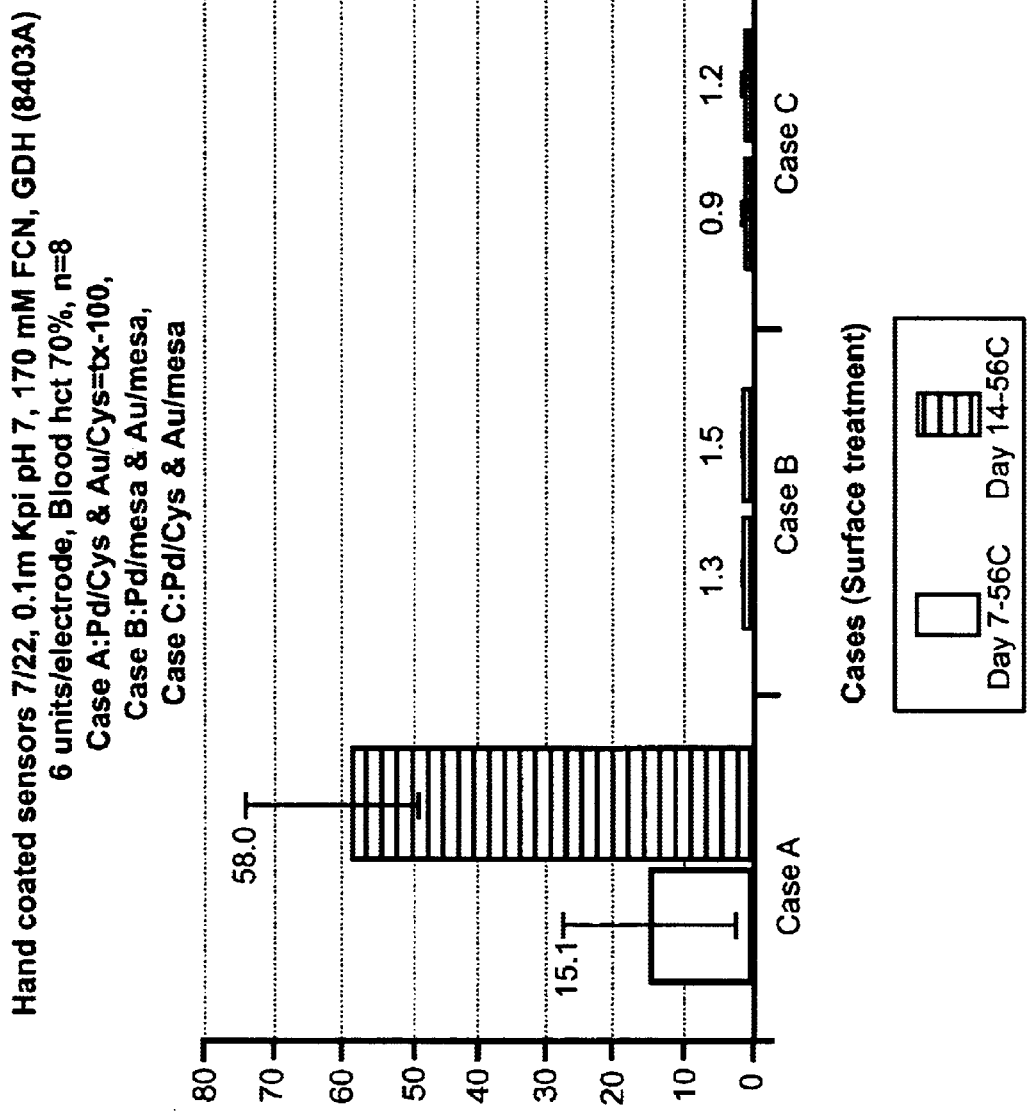

ELECTROCHEMICAL TEST STRIP FOR USE IN ANALYTE DETERMINATION

INTRODUCTION

1. Field of the Invention

The field of this invention is analyte determination, particularly electrochemical analyte determination and more particularly the electrochemical determination of blood analytes.

2. Background

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a reaction zone in an electrochemical cell comprising two electrodes, i.e. a reference and working electrode, where the electrodes have an impedance which renders them suitable for amperometric measurement. The component to be analyzed is allowed to react directly with an electrode, or directly or indirectly with a redox reagent to form an oxidizable (or reducible) substance in an amount corresponding to the concentration of the component to be analysed, i.e. analyte. The quantity of the oxidizable (or reducible) substance present is then estimated electrochemically and related to the amount of analyte present in the initial sample.

In electrochemical analyte detectors used to practice the above described methods, it is often desirable to modify the surface of the metal electrodes to be hydrophilic. A variety of different techniques have been developed to modify the surfaces of metal electrodes. However, such surface modified electrodes tend to have limited storage life, thus limiting their potential applications.

As such, there is continued interest in the identification of new methods for modifying metallic electrode surfaces for use in the electrochemical detection of analytes. Of particular interest would be the development of a method which resulted in a storage stable hydrophilic surface that provided rapid wicking time and did not interfere with the electrochemical measurements of the electrode.

Relevant Literature

U.S. Patent documents of interest include: U.S. Pat. Nos. 5,834,224; 5,942,102 and 5,972,199. Other patent documents of interest include WO 99/49307; WO 97/18465 and GB 2 304 628. Other references of interest include: Dalmia et al, J. Electroanalytical Chemistry (1997) 430: 205–214; Nakashima et al., J. Chem. Soc. (1990) 12: 845–847; and Palacin et al., Chem. Mater. (1996) 8:1316–1325.

SUMMARY OF THE INVENTION

Electrochemical test strips and methods for their use in the detection of an analyte, e.g. glucose, in a physiological sample, e.g. blood, are provided. The subject test strips have a reaction area defined by opposing metal electrodes separated by a thin spacer layer. The metal surface of at least one of the electrodes is modified by a homogenous surface modification layer made up of linear self-assembling molecules having a first sulfhydryl end group and a second sulfonate end group separated by a short chain alkyl linking group, where 2-mercaptoethane sulfonic acid or a salt thereof is preferred in certain embodiments. The subject electrochemical test strips find application in the detection of a wide variety of analytes, and are particularly suited for use the detection of glucose.

BRIEF DESCRIPTION OF THE FIGURES

FIG. 3 provides an analysis of the contact angle of various cystine treated metallic electrodes at various times following treatment.

FIG. 4 provides an analysis of the wicking time of various cystine treated metallic electrodes at various times following treatment.

FIG. 7 provides a comparison of the wicking time of various cystine and MESA coated electrodes.

DESCRIPTION OF THE SPECIFIC EMBODIMENTS

Electrochemical test strips for use in analyte detection in a physiological sample are provided. In the subject test strips, two opposing metal electrodes separated by a thin spacer layer define a reaction area. A critical feature of the subject test strips is that at least one of the metal electrodes has a surface that is modified with a surface modification layer made up of linear molecules having a sulfhydryl end group and a sulfonate end group separated by a lower alkyl linking group. Present in the reaction area are redox reagents comprising an enzyme and a mediator. Also provided are methods of using the subject test strips in analyte detection, e.g. glucose determination. In further describing the subject invention, the electrochemical test strip will be described first, followed by a more in depth review of the subject methods for using the test strips in analyte detection.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

Electrochemical Test Strips

Figure 1:
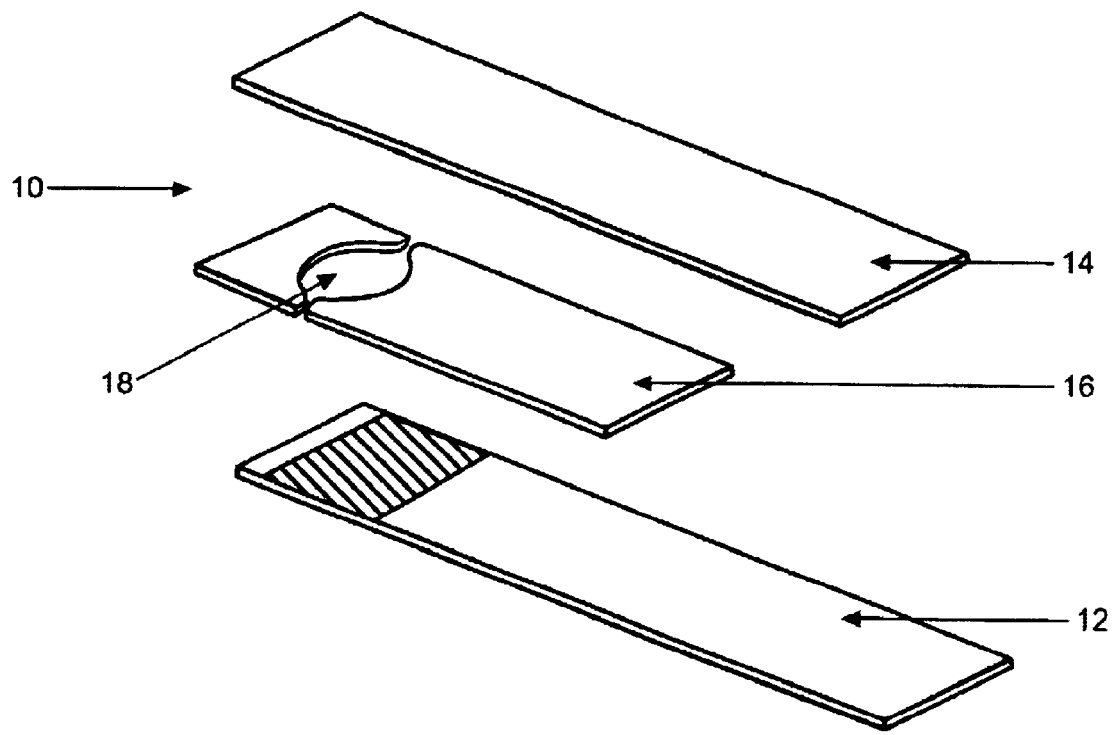
FIGS. 1 and 2 provide a representation of an electrochemical test strip according to the subject invention.
Figure 2:
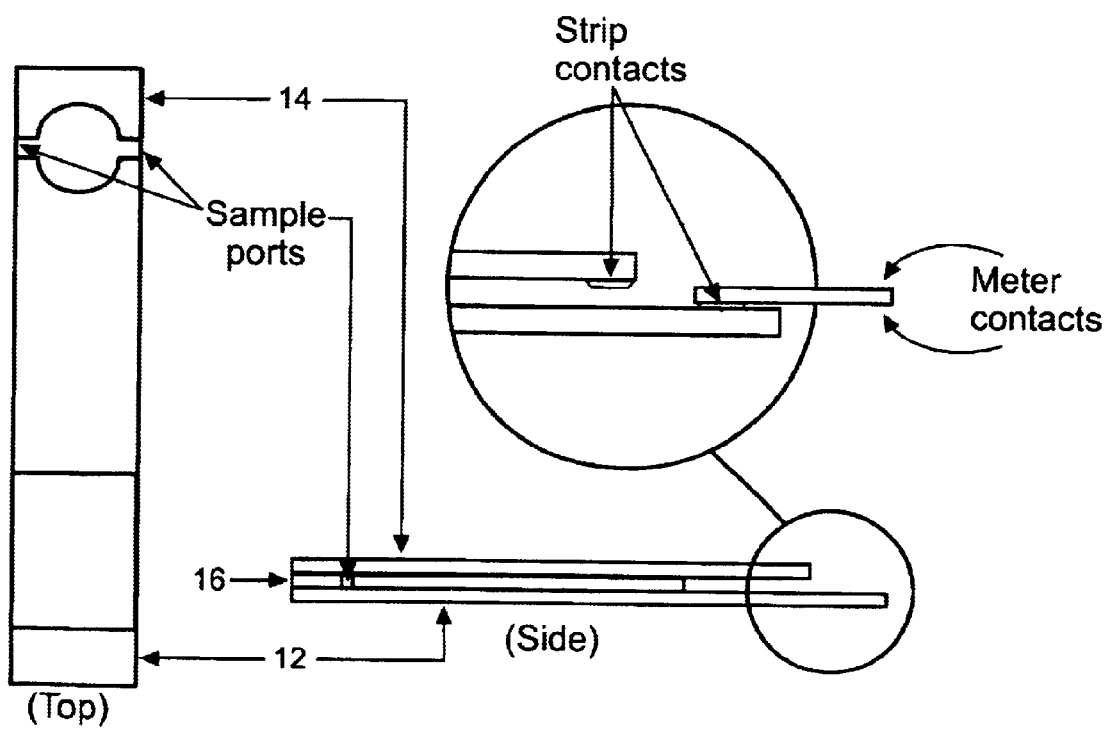

As summarized above the electrochemical test strips of the subject invention are made up of two opposing metal electrodes separated by a thin spacer layer, where these components define a reaction area in which is located a redox reagent system. A representation of an electrochemical test strip according to the subject invention is provided in FIGS. 1 and 2. Specifically, FIG. 1 provides an exploded view of an electrochemical test strip 10 which is made up of working electrode 12 and reference electrode 14 separated by spacer layer 16 which has a cutaway section 18 that defines the reaction zone or area in the assembled strip. FIG. 2 shows the same test strip in assembled form. Each of the above elements, i.e. the working and reference electrodes, the spacer layer and the reaction area are now described separately in greater detail.

Electrodes

As indicated above, the subject electrochemical test strips include a working electrode and a reference electrode. Generally, the working and reference electrodes are configured in the form of elongated rectangular strips. Typically, the length of the electrodes ranges from about 1.9 to 4.5 cm, usually from about 2 to 2.8 cm. The width of the electrodes ranges from about 0.38 to 0.76 cm, usually from about 0.51 to 0.67 cm. The reference electrodes typically have a thickness ranging from about 10 to 100 nm and usually from about 18 to 22 nm. In certain embodiments, the length of one of the electrodes is shorter than the length of the other electrode, wherein in certain embodiments it is about 0.32 cm shorter.

The working and reference electrodes are further characterized in that at least the surface of the electrodes that faces the reaction area in the strip is a metal, where metals of interest include palladium, gold, platinum, silver, iridium, carbon, doped indium tin oxide, stainless steel and the like. In many embodiments, the metal is gold or palladium. While in principle the entire electrode may be made of the metal, each of the electrodes is generally made up of an inert support material on the surface of which is present a thin layer of the metal component of the electrode. In these more common embodiments, the thickness of the inert backing material typically ranges from about 51 to 356 µm, usually from about 10 to 153 µm while the thickness of the metal layer typically ranges from about 10 to 100 nm and usually from about 20 to 40 nm, e.g. a sputtered metal layer. Any convenient inert backing material may be employed in the subject electrodes, where typically the material is a rigid material that is capable of providing structural support to the electrode and, in turn, the electrochemical test strip as a whole. Suitable materials that may be employed as the backing substrate include plastics, e.g. PET, PETG, polyimide, polycarbonate, polystyrene, silicon, ceramic, glass, and the like.

The subject test strips are further characterized in that at least one of the metallic surfaces of the electrodes, and in some embodiments both of the metallic surfaces of the electrodes, that face, i.e. border or bound, the reaction area, have a surface modification layer present thereon. The surface modification layer is a homogenous layer of self-assembling molecules that renders the surface stably hydrophilic in a storage stable manner. More specifically, the surface modification layer should impart to the surface a low contact angle, typically ranging from about 10 to 30 and usually from about 15 to 25° and a fast wicking time, e.g. 0.5 to 2 and usually from about 1 to 2 s, even after an extended period of time at an elevated temperature, e.g. even after 7 to 14 days at a temperature of from about 4 to 56° C.

By homogenous is meant that the surface modification layer is made up of the same type of molecules. In other words, all of the self-assembling molecules in the surface modification layer are identical. Generally, the self-assembling molecule that makes up the surface modification layer is a linear molecule having a sulfhydryl end group and a sulfonate end group separated by a lower alkyl linking group. The term sulfonate end group is used herein to refer to both a sulfonic acid moiety as well as a sulfonate moiety, which may be associated with a cation, e.g. sodium, as is found in a sulfonate salt. The alkyl linking group generally ranges from about 1 to 8, usually from about 1 to 6 carbon atoms in length, and may or may not include one or more sites of unsaturation, but is generally a saturated molecule. In certain embodiments, the number of carbon atoms in the alkyl linking group ranges from about 1 to 4 and often from about 1 to 3, with methylene and ethylene linking groups being common in these embodiments.

In many embodiments, the molecule that makes up the self-assembling surface modification layer is a molecule of the formula:

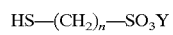

wherein:

n is an integer from 1 to 6; and

Y is H or a cation.

Of particular interest in many embodiments of the subject invention are surface modification layers made up of 2-mercaptoethane ethane sulfonic acid or a salt thereof, e.g. 2-mercaptoethane sulfonate sodium.

The working and reference electrodes as described above may be fabricated using any convenient protocol. A representative protocol includes preparation of the metal electrodes by first sputtering the metal layer of sufficient thickness onto the surface of the inert backing material. Next, the electrode(s) to be surface modified, or at least the metallic surface that is to be modified, to have the surface modification layer is contacted with a fluid composition, e.g. an aqueous organic solution, of the self-assembling molecule. Contact may be achieved by any convenient means, including submersion slot coating, grevure printing of the electrode into the composition. The concentration of the self-assembling molecule in the fluid composition typically ranges from about 0.5 to 1%, usually from about 0.05 to 0.5% and more usually from about 0.05 to 0.3%. Contact is maintained for a sufficient period of time for the monolayer to form, e.g. for a period of time ranging from about 0.5 to 3 minutes, usually from about 0.5 to 2 min, followed by drying of the electrode surface for use in the subject electrochemical test strips. A more detailed representative fabrication profile is provided in the experimental section, infra.

Spacer Layer

A feature of the subject electrochemical test strips is that the working and reference electrodes as described above face each other and are separated by only a short distance, such that the distance between the working and reference electrode in the reaction zone or area of the electrochemical test strip is extremely small. This minimal spacing of the working and reference electrodes in the subject test strips is a result of the presence of a thin spacer layer positioned or sandwiched between the working and reference electrodes. The thickness of this spacer layer generally ranges from about 1 to 500 um, usually from about 102 to 153 um. The spacer layer is cut so as to provide a reaction zone or area with at least an inlet port into the reaction zone, and generally an outlet port out of the reaction zone as well. A representative spacer layer configuration can be seen in FIGS. 1 and 2. While the spacer layer is shown in these figures as having a circular reaction area cut with side inlet and outlet vents or ports, other configurations are possible, e.g. square, triangular, rectangular, irregular shaped reaction areas, etc. The spacer layer may be fabricated from any convenient material, where representative suitable materials include PET, PETG, polyimide, polycarbonate and the like, where the surfaces of the spacer layer may be treated so as to be adhesive with respect to their respective electrodes and thereby maintain the structure of the electrochemical test strip. Of particular interest is the use of a die-cut double-sided adhesive strip as the spacer layer.

Reaction Zone

The subject electrochemical test strips include a reaction zone or area that is defined by the working electrode, the reference electrode and the spacer layer, where these elements are described above. Specifically, the working and reference electrodes define the top and bottom of the reaction area, while the spacer layer defines the walls of the reaction area. The volume of the reaction area is at least about 0.1 μl, usually at least about 1 μl and more usually at least about 1.51 μl, where the volume may be as large as 10 μl or larger. As mentioned above, the reaction area generally includes at least an inlet port, and in many embodiments also includes an outlet port. The cross-sectional area of the inlet and outlet ports may vary as long as it is sufficiently large to provide an effective entrance or exit of fluid from the reaction area, but generally ranges from about $9 \times 10^{-5}$ to $5 \times 10^{-3}$ cm$^2$, usually from about $1.3 \times 10^{-3}$ to $2.5 \times 10^{-3}$ cm$^2$.

Present in the reaction area is a redox reagent system, which reagent system provides for the species that is detected by the electrode and therefore is used to derive the concentration of analyte in a physiological sample. The redox reagent system present in the reaction area typically includes at least an enzyme(s) and a mediator. In many embodiments, the enzyme member(s) of the redox reagent system is an enzyme or plurality of enzymes that work in concert to oxidize the analyte of interest. In other words, the enzyme component of the redox reagent system is made up of a single analyte oxidizing enzyme or a collection of two or more enzymes that work in concert to oxidize the analyte of interest. Enzymes of interest include oxidases, dehydrogenases, lipases, kinases, diaphorases, quinoproteins and the like.

The specific enzyme present in the reaction area depends on the particular analyte for which the electrochemical test strip is designed to detect, where representative enzymes include: glucose oxidase, glucose dehydrogenase, cholesterol esterase, cholesterol oxidase, lipoprotein lipase, glycerol kinase, glycerol-3-phosphate oxidase, lactate oxidase, lactate dehydrogenase, pyruvate oxidase, alcohol oxidase, bilirubin oxidase, uricase, and the like. In many preferred embodiments where the analyte of interest is glucose, the enzyme component of the redox reagent system is a glucose oxidizing enzyme, e.g. a glucose oxidase or glucose dehydrogenase.

The second component of the redox reagent system is a mediator component, which is made up of one or more mediator agents. A variety of different mediator agents are known in the art and include: ferricyanide, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, ruthenium complexes and the like. In those embodiments where glucose in the analyte of interest and glucose oxidase or glucose dehydrogenase are the enzyme components, mediator of particular interest is ferricyanide. Other reagents that may be present in the reaction area include buffering agents, e.g. citraconate, citrate, phosphate, "Good" buffers and the like.

The redox reagent system is generally present in dry form. The amounts of the various components may vary, where the amount of enzyme component typically ranges from about 0.1 to 10% by weight.

Methods

Also provided by the subject invention are methods of using the subject electrochemical test strips to determine the concentration of an analyte in a physiological sample. A variety of different analytes may be detected using the subject test strips, where representative analytes include glucose, cholesterol, lactate, alcohol, and the like. In many preferred embodiments, the subject methods are employed to determine the glucose concentration in a physiological sample. While in principle the subject methods may be used to determine the concentration of an analyte in a variety of different physiological samples, such as urine, tears, saliva, and the like, they are particularly suited for use in determining the concentration of an analyte in blood or blood fractions, and more particularly in whole blood.

In practicing the subject methods, the first step is to introduce a quantity of the physiological sample into the reaction area of the test strip, where the electrochemical test strip is described supra. The amount of physiological sample, e.g. blood, that is introduced into the reaction area of the test strip may vary, but generally ranges from about 0.1 to 10 ul, usually from about 1 to 1.6 ul. The sample may be introduced into the reaction area using any convenient protocol, where the sample may be injected into the reaction area, allowed to wick into the reaction area, and the like, as may be convenient.

Following application of the sample to the reaction zone, an electrochemical measurement is made using the reference and working electrodes. The electrochemical measurement that is made may vary depending on the particular nature of the assay and the device with which the electrochemical test strip is employed, e.g. depending on whether the assay is coulometric, amperometric or potentiometric. Generally, the electrochemical measure will measure charge (coulometric), current (amperometric) or potential (potentiometric), usually over a give period of time following sample introduction into the reaction area. Methods for making the above described electrochemical measurement are further described in U.S. Pat. Nos. 4,224,125; 4,545,382; and 5,266,179; as well as WO 97//18465; WO 99/49307; the disclosures of which are herein incorporated by reference.

Following detection of the electrochemical signal generated in the reaction zone as described above, the amount of the analyte present in the sample introduced into the reaction zone is then determined by relating the electrochemical signal to the amount of analyte in the sample. In making this derivation, the measured electrochemical signal is typically compared to the signal generated from a series of previously obtained control or standard values, and determined from this comparison. In many embodiments, the electrochemical signal measurement steps and analyte concentration derivation steps, as decribed above, are performed automatically by a devices designed to work with the test strip to produce a value of analyte concentration in a sample applied to the test strip. A representative reading device for automatically practicing these steps, such that user need only apply sample to the reaction zone and then read the final analyte concentration result from the device, is further described in copending U.S. application Ser. No. 09/333,793, now U.S. Pat. No. 6,193,873 B1, entitled "Sample Detection to Initiate Timing of an Electrochemical Assay," the disclosure of which is herein incorporated by reference.

Kits

Also provided by the subject invention are kits for use in practicing the subject methods. The kits of the subject invention at least include an electrochemical test strip with at least one surface modified metal electrode, as described above. The subject kits may further include a means for obtaining a physiological sample. For example, where the physiological sample is blood, the subject kits may further include a means for obtaining a blood sample, such as a lance for sticking a finger, a lance actuation means, and the like. In addition, the subject kits may include a control solution, e.g. a glucose control solution that contains a standardized concentration of glucose. In certain embodiments, the kits also comprise an automated instrument, as described above, for detecting an electrochemical signal using the electrodes following sample application and relating the detected signal to the amount of analyte in the sample. Finally, the kits include instructions for using the subject reagent test strips in the determination of an analyte concentration in a physiological sample. These instructions may be present on one or more of the packaging, a label insert, containers present in the kits, and the like.

The following examples are offered by way of illustration and not by way of limitation.

EXPERIMENTAL

I. Preparation of Electrochemical Test Strips

A. Preparation of MESA Treated Electrochemical Test Strips

A (0.1)1% 2-mercaptoethane sulfonic acid (MESA) solution is prepared by dissolving 1.000 gm MESA (TCI, Catalog #M0913) into 999 gm Milli Q water. Gold and palladium sheets are prepared by sputtering the surface of a 7 mil thick polyester substrate with gold or palladium such that a surface metallic layer of 100 to 500 angstroms is obtained. Following preparation of these gold and palladium master rolls, 12 in×8.5 inch sheets are cut. The sheets are then immersed in the 1% MESA solution for 1 minute. The coated sheet is then air dried for 1 hour and tested for contact angle using a Goniometer and water as described in Procedure A found in Appendix A, infra, to ensure that the contact angle is <20°.

Test strips having dimensions of 0.2×1.2 inch are then cut from the above gold and metal sheets and are used to fabricate electrochemical test strips as follows. A gold strip and palladium strip are used to sandwich a die-cut double sided pressure sensitive adhesive strip having a thickness of 0.005 in and a circular die-cut area that defines the reaction zone, inlet and outlet ports when sandwiched between the gold and metal strips, as shown in FIGS. 1 and 2. A dry reagent consisting of buffer, mediator, enzyme and bulking agents is ink jetted onto the palladium electrode prior to sandwiching the double-sided adhesive.

B. Preparation of Cystine Treated Electrochemical Test Strips

Cystine treated electrochemical test strips were prepared according to a standard industry protocol.

II. Characterization of Cystine Treated Electrochemical Test Strips

A. Contact Angle

The contact angle of cystine treated gold and palladium test strips was determined with water and a goniometer as described in Procedure B found in Appendix A, infra. The contact angle was determined at various times following surface treatment, i.e. 0, 7 and 14 days following treatment, and at various storage temperatures, e.g. room temperature and 56° C. The results are provided in FIG. 3.

B. Wicking Time

The wicking time of cystine treated gold and palladium test strips was determined as described in Procedure C found in Appendix A, infra. The wicking time was determined at various times following surface treatment, i.e. 0, 7 and 14 days following treatment, and at various storage temperatures, e.g. room temperature and 56° C. The results are provided in FIG. 4.

III. Characterization of MESA Treated Electrochemical Test Strips

A. Contact Angle

Figure 5A:
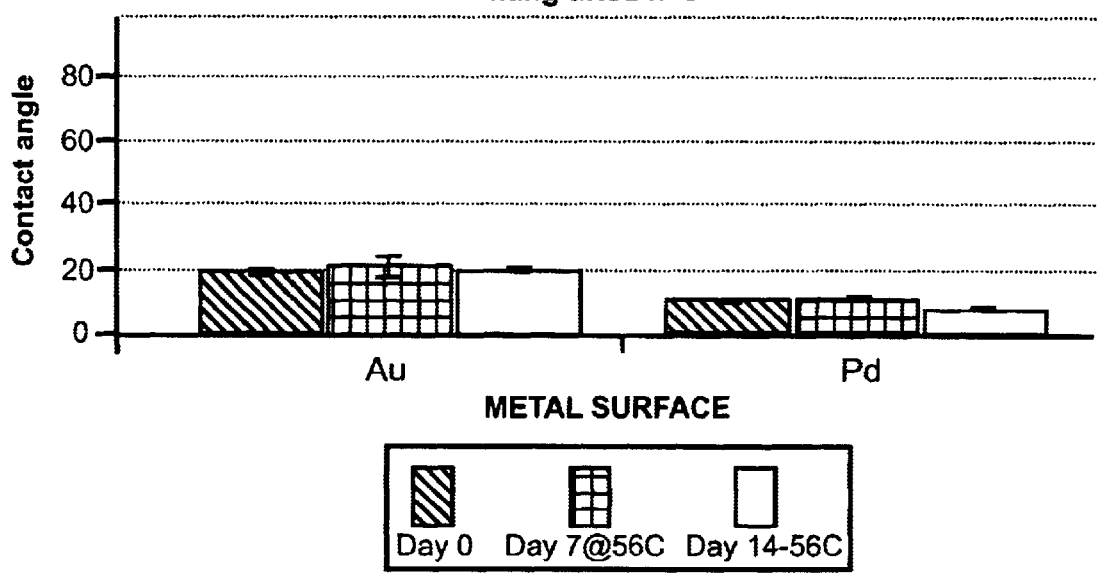
FIGS. 5A and 5B provide an analysis of the contact angle of various MESA treated metallic electrodes at various times following treatment.
Figure 5B:
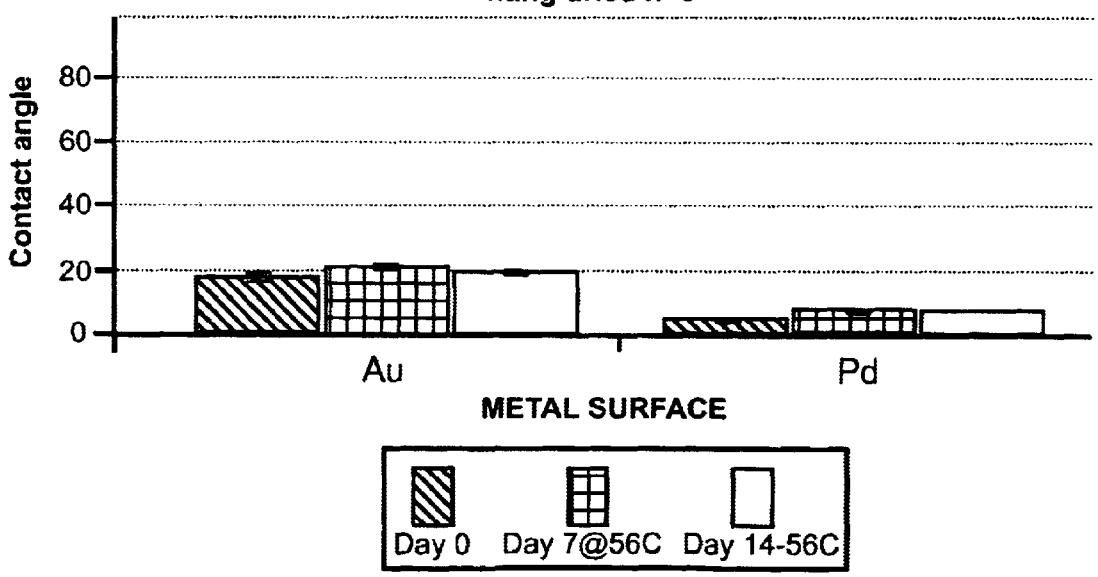

The contact angle of MESA treated gold and palladium test strips (treated at pH 5.4 and 11.5) was determined with water and a goniometer as described in Procedure B found in Appendix A, infra. The contact angle was determined at various times following surface treatment, i.e. 0, 7 and 14 days following treatment where the storage temperature was 56° C. The results are provided in FIGS. 5A (pH 5.4) and 5B (pH 11.5).

B. Wicking Time

Figure 6:
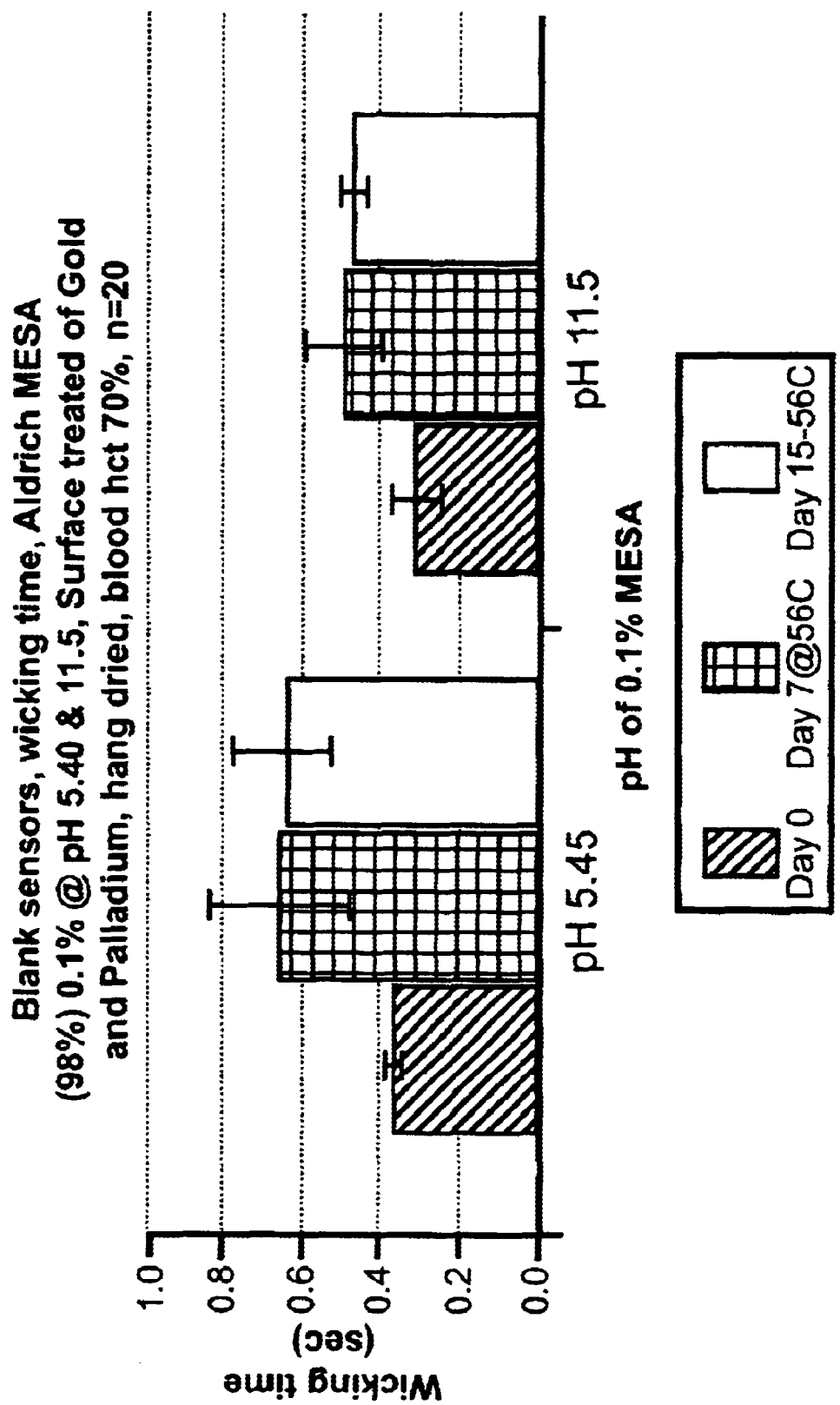
FIG. 6 provides an analysis of the wicking time of various MESA treated metallic electrodes at various times following treatment.

The wicking time of MESA treated gold and palladium test strips (treated at pH 5.4 and 11.5) was determined as described in Procedure B found in Appendix A, infra. The wicking time was determined at various times following surface treatment, i.e. 0, 7 and 15 days following treatment, and at various storage temperatures, e.g. room temperature and 56° C. The results are provided in FIG. 6.

IV. Wicking Time Comparison Study

The wicking time of three different electrochemical test strips prepared as described above was compared. The first electrochemical test strip (Case A) was one in which both the gold and palladium surfaces were cystine treated. The second electrochemical test strip (Case B) was one in which both the palladium and gold surfaces were treated with MESA. The third electrochemical test strip (Case C) was one in which the palladium surface was cystine treated and the gold surface was MESA treated. Wicking times were determined as described in Procedure C found in Appendix A, infra, on strips stored in SureStep® vials at 56° C. for 7 and 14 days, and the results are provided in FIG. 7.

The above results and discussion demonstrate that significantly improved electrochemical test strips for use in the determination of an analyte in a test sample are provided by the subject invention. Specifically, storage stable electrochemical test strips having durable hydrophilic surfaces that exhibit low interference to the electrochemical measurement of oxidized species and have fast wicking times are provided. Furthermore, the surface modifying reagents used to modify the surfaces of the subject test strips are odorless. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be

Appendix A

Procedure A

Surface Treatment Procedure for Gold and Palladium Metallized Plastics

| | |
|---|---|
| Materials: | 1. Pyrex glass baking dish size 4 Q (10.5" × 14.75" × 2.25") |
| | 2. Mill-Q Water |
| | 3. Stop watch |
| | 4. Gold and Palladium sheets size 12" × 8.5" |
| Chemical: | 2-mercaptoethane sulfonic acid, sodium salt |
| | Manufacturer TCI |
| | Catalog # M0913 |
| | Purity: 99% |
| | Molecular Wt. 164.18 |
| Procedure: | 0.1% (w/w)MESA |
| | 1. Weigh out 1.000(±0.0005) g of 2-mercaptoethane sulfonic acid sodium in a weighing paper. |
| | 2. Weigh out 999.0(±0.1) g of Milli Q water in a glass beaker. |
| | 3. Add MESA powder slowly to the beaker. Let it dissolve completely |
| Surface Treatment: | 4. Cut out Gold and Palladium sheets (size 12" × 8.5") from the roll. |
| | 5. Pour out the content of beaker to the baking dish slowly. |
| | 6. Coat metal sheets one by one, metal layer facing dish bottom. Make sure sheet is completely covered with solution. Use the stopwatch to monitor coating time (1 min/sheet). |
| | 7. Drying time is about 1 hr. |
| | 8. Check the contact angle of Metallized film with water by Goniometer. Contact angle should be <20° for Au and Pd surfaces. |

Procedure B

Contact angle measurement using Rame-Hart Goniometer

| | |
|---|---|
| Materials: | 1. MESA coated Gold and Palladium sheet |
| | 2. Rame-Hart Goniometer Model-100-00-115 |
| | 3. Automated Pipetting system |
| | 4. Software RHI 2001 |
| Procedure: | Using water, fill up the Automated Pipette system. Place the sample (Au/Pd) on the sample platform and hold with clamp. Open RHI 2001 program and set up the baseline. Drop 3 to 5 uL of water from automatic pipette. RHI 2001 system captures the image and measure the contact angle from both sides and averages them. This can be repeated for several times. |

Procedure C

Wicking time measurement

| | |
|---|---|
| Material: | 1. MESA treated test strips |
| | 2. Fresh blood adjusted to 70% Hematocrit |
| | 3. Pipette- 20 uL |
| | 4. Pieces of Parafilm for blood application. |
| | 5. Panasonic camera model GP KP222 |
| | 6. Adobe Premiere software 4.2 for video capture |
| | 7. Computer System and a Monitor |
| | 8. Two side adhesive tape & a platform for strip |
| Procedure: | 1. Place a strip on a platform and hold it with tape. |
| | 2. Place the strip under the camera lens and adjust the focus and magnification. |
| | 3. Launch the Premiere software and open movie captures program. Select 30fps NTSC system for capturing live movie. |
| | 4. Place 5 uL of 70% hct blood on Parafilm surface. |
| | 5. Turn on recording mode and apply blood from either side of test strip in to the capillary. |
| | 6. Turn off the recording mode when blood reaches the other end of test strip |
| | 7. Go to the image window and analyze it. Use In mark when blood touches the strip and out mark when blood reaches the other end. Software does the frames count (30 frames/seconds) and displays in lower window. |
| | 8. To calculate wicking time, divide number of frames with 30. |
| | 9. Repeat the procedure for # of strips |

What is claimed is:

1. An electrochemical test strip comprising:

(a) a reaction zone defined by opposing working and reference electrodes separated by a spacer layer, wherein at least one of said working and reference electrodes has a surface modified with a homogenous surface modification layer made up of self assembling molecules having a first sulfhydryl end group and a second sulfonate end group, wherein said sulfhydryl and sulfonate end groups are separated by a lower alkyl linker group wherein all the self-assembling molecules are identical; and (b) a redox reagent system present in said reaction zone, wherein said redox reagent system comprises at least one enzyme and a mediator.

2. The electrochemical test strip according to claim 1, wherein at least one of said electrodes comprises a metal selected from the group consisting of: gold, palladium, silver, iridium, carbon, doped indium tin oxide and stainless steel.

3. The electrochemical test strip according to claim 2, wherein said electrode comprises gold or palladium.

4. The electrochemical test strip according to claim 1, wherein said self-assembling molecules have the formula:

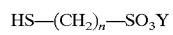

wherein:

n is an integer from 1 to 6; and

Y is H or a cation.

5. The electrochemical test strip according to claim 1, wherein said at least one enzyme includes an oxidizing enzyme.

6. An electrochemical test strip comprising:

(a) a reaction zone defined by opposing working and reference electrodes comprising a metal surface separated by a thin spacer layer, wherein at least one of said working and reference electrodes has a surface modified with a homogenous surface modification layer made up of self assembling molecules wherein all the self-assembling molecules are identical of the formula:

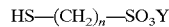

wherein:

n is an integer from 1 to 6; and

Y is H or a cation; and (b) a redox reagent system present in said reaction zone, wherein said redox reagent system comprises enzymes and a mediator.

7. The electrochemical test strip according to claim 6, wherein said reaction zone has a volume ranging from about 0.1 to 10 μl.

8. The electrochemical test strip according to claim 6, wherein said metal is selected from the group consisting of gold and palladium.

9. The electrochemical test strip according to claim 6, wherein said enzymes include an oxidizing enzyme.

10. The electrochemical test strip according to claim 9, wherein said oxidizing enzyme is a glucose oxidizing enzyme.

11. The electrochemical test strip according to claim 6, wherein said self assembling molecule is 2-mercaptoethane sulfonic acid or a salt thereof.

12. An electrochemical test strip for use in detecting the concentration of glucose in a physiological sample, said test strip comprising:
(a) a reaction zone defined by opposing working and reference electrodes each comprising a metal surface selected from the group consisting of gold and palladium separated by a thin spacer layer, wherein at least one of said working and reference electrodes has a surface modified with a homogenous surface modification layer made up of 2-mercaptoethane sulfonic acid or a salt thereof wherein all the self-assembling molecules are identical; and
(b) a redox reagent system present in said reaction zone, wherein said redox reagent system comprises a glucose oxidizing enzyme and a mediator.

13. The electrochemical test strip according to claim 12, wherein said reaction zone has a volume ranging from about 0.1 to 10 μl.

14. The electrochemical test strip according to claim 12, wherein said reference electode is a gold electrode.

15. The electrochemical test strip according to claim 12, wherein said working electrode is a palladium electrode.

16. A method of determining the concentration of an analyte in a physiological sample, said method comprising:
(a) applying said physiological sample to an electrochemical test strip comprising:
(i) a reaction zone defined by opposing working and reference metallic electrodes separated by a spacer layer, wherein at least one of said metallic working and reference electrodes has a surface modified with a homogenous surface modification layer made up of self assembling molecules having a first sulfhydryl end group and a second sulfonate and group, wherein said, sulfhydryl and sulfonate end groups are separated by a lower alkyl linker group wherein all the self-assembling molecules are identical; and
(ii) a redox reagent system present in said reaction zone, wherein said redox reagent system comprises at least one enzyme and a mediator;
(b) detecting an electrical signal in said reaction zone using said metallic electrodes; and
(c) measuring said detected electrical signal to thereby determine the concentration of said analyte in said sample.

17. The method according to claim 16, wherein said self-assembling molecules have the formula:

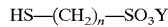

wherein:

n is an integer from 1 to 6; and

Y is H or a cation.

18. The method according to claim 17, wherein said self-assembling molecules are 2-mercaptoethane sulfonic acid or a salt thereof.

19. The method according to claim 16, wherein said analyte is glucose.

20. The method according to claim 19, wherein said redox reagent system comprises a glucose oxidizing enzyme.

21. The elestrochemical test strip according to claim 1, wherein said strip is present in an automated instrument designed to work with test strips.

22. The method according to claim 16, wherein said detecting and measuring steps are performed by an automated instrument designed to work with test strips.

* * * * *